(12) United States Patent
Ryu

(10) Patent No.: US 7,288,686 B2
(45) Date of Patent: Oct. 30, 2007

(54) HYDROGENATION CATALYST AND HYDROGENATION PROCESS

(75) Inventor: J. Yong Ryu, League City, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 24 days.

(21) Appl. No.: 10/912,252

(22) Filed: Aug. 5, 2004

(65) Prior Publication Data

US 2005/0010070 A1    Jan. 13, 2005

Related U.S. Application Data

(62) Division of application No. 09/977,666, filed on Oct. 15, 2001, now abandoned.

(51) Int. Cl.
| | |
|---|---|
| C07C 5/03 | (2006.01) |
| C07C 5/05 | (2006.01) |
| C07C 5/08 | (2006.01) |

(52) U.S. Cl. .................. 585/259; 502/257; 502/258; 502/260; 502/271; 502/272; 502/273

(58) Field of Classification Search ............... 585/250, 585/257, 258, 259, 260, 271, 272, 273
See application file for complete search history.

(56) References Cited

U.S. PATENT DOCUMENTS

| | | | | |
|---|---|---|---|---|
| 2,620,314 | A | 12/1952 | Hoekstra | 252/448 |
| 4,174,355 | A | 11/1979 | Patel et al. | 585/843 |
| 4,179,408 | A | 12/1979 | Sanchez et al. | 252/448 |
| 4,273,735 | A | 6/1981 | Jacques et al. | 264/5 |
| 4,440,956 | A | 4/1984 | Couvillion | 585/260 |
| 4,493,906 | A | 1/1985 | Couvillion | 502/346 |
| 4,533,779 | A | 8/1985 | Boitiaux et al. | 585/259 |
| 4,831,200 | A | 5/1989 | Debras et al. | 585/259 |
| 5,258,340 | A * | 11/1993 | Augustine et al. | 502/60 |
| 5,488,024 | A * | 1/1996 | Cheung et al. | 178/18.07 |
| 5,510,568 | A | 4/1996 | Hearn | 585/834 |
| 5,595,643 | A | 1/1997 | Torimoto et al. | 205/634 |
| 5,597,476 | A | 1/1997 | Hearn et al. | 208/208 R |
| 5,714,644 | A * | 2/1998 | Irgang et al. | 568/857 |
| 5,807,477 | A | 9/1998 | Hearn et al. | 208/238 |
| 5,877,363 | A | 3/1999 | Gildert et al. | 585/260 |
| 5,899,678 | A * | 5/1999 | Thomson et al. | 431/2 |
| 5,958,825 | A * | 9/1999 | Wulff-Doring et al. | 502/300 |
| 6,127,310 | A * | 10/2000 | Brown et al. | 502/339 |
| 6,204,218 | B1 * | 3/2001 | Flick et al. | 502/243 |
| 6,239,322 | B1 * | 5/2001 | Didillon et al. | 585/260 |
| 6,350,717 | B1 * | 2/2002 | Frenzel et al. | 502/330 |
| 6,417,136 | B2 * | 7/2002 | Cheung et al. | 502/330 |
| 6,437,206 | B1 * | 8/2002 | Meyer et al. | 585/260 |
| 6,509,292 | B1 * | 1/2003 | Blankenship et al. | 502/330 |

FOREIGN PATENT DOCUMENTS

| | | |
|---|---|---|
| DE | 2109070 | 2/1970 |
| DE | 2412191 | 3/1973 |
| FR | 1253947 | 1/1961 |

* cited by examiner

*Primary Examiner*—Elizabeth D. Wood
(74) *Attorney, Agent, or Firm*—Osha Liang LLP

(57) ABSTRACT

A supported hydrogenation catalyst comprising (1) Pd or a Group 8 metal comprising Pd and one other Group 8 metal, preferably a Group 8 metal selected from Pt, Ir, Ru, Co or Ni, and (2) at least two metals selected from Ag, Zn or Bi, preferably Ag and at least one of Zn or Bi. Optionally the catalyst may contain K. The catalyst is supported on a porous support such as a silica, alumina, silica-alumina or carbon. The preferred supports have an average pre diameter of 180 Å with no pores smaller than 35 Å, total pore volume larger than 0.65 cc/g and preferably less than about 100 $m^2/g$ BET surface area. The catalysts are useful for the hydrogenation of unsaturated hydrocarbons such as acetylenes and diolefins in various mixed olefin streams.

8 Claims, No Drawings

HYDROGENATION CATALYST AND HYDROGENATION PROCESS

This is a division of aplication Ser. No. 09/977,666 filed on Oct. 15, 2001 and now abandoned. The present invention relates to multi component catalyst forthe hydrogenation of the highly unsaturated compounds comprising Pd and a selected group of modifiers on supports having particular characteristics and process of the hydrogenation of unsaturated hydrocarbons and more particularly the selective hydrogenation of highly unsaturated hydrocarbons such as acetylenes. More particularly the invention relates to the selective hydrogenation of acetylenic compounds in $C_2$-$C_4$ mixed olefin streams.

BACKGROUND OF THE INVENTION

1. Field of the Invention

The present invention relates to multi component catalyst for the hydrogenation of the highly unsaturated compounds comprising Pd and a selected group of modifiers on supports having particular characteristics and process of the hydrogenation of unsaturated hydrocarbons and more particularly the selective hydrogenation of highly unsaturated hydrocarbons such as acetylenes. More particularly the invention relates to the selective hydrogenation of acetylenic compounds in $C_2$-$C_4$ mixed olefin streams.

2. Related Information

Supported palladium and nickel catalysts have been used for various hydrogenation processes for a considerable period of time. Such processes include the selective hydrogenation of acetylenic compounds and dienes in various mixed olefins streams and gasoline and the hydrogenation of benzene.

German patent 2,412,191 discloses the purification of 1,3-butadiene and isoprene streams by the selective hydrogenation of acetylenic compounds using finely dispersed catalyst or supported catalyst. The preferred catalyst metal is either a noble metal such as Pd or non-noble metal such as Co, Fe or Mo. The improvement claimed is that the use of cylcopentadiene improves the 1,3-butadiene selectivity with either noble or non noble catalyst.

It has been well documented that supported Pd catalysts are unstable for selective hydrogenation of vinyl acetylene due to the formation of complex compounds of vinyl acetylene with Pd. The Pd complex compounds are soluble in the hydrocarbon stream. It has been found that the addition of silver to the Pd catalyst results in the stabilization of the catalyst deactivation caused by the loss of Pd metal and an improvement in the selectivity of desired olefin product. See M. L. Derrien et al, *Studies in Surface Science and Catalysis*, Vol 27, page 613 (1986), and Elsvier and K. James Sasaki, *Petrochemicals and Gas Processing*, 113 PTQ Autumn, 1997.

U.S. Pat. No. 4,533,779 discloses palladium-gold catalyst supported on supports such as alumina (1 to 100 $m^2$/g) for selective hydrogenation of acetylenic compounds. The alumina used in the examples had a surface area of 70 $m^2$/g, a total pore volume of 0.6 cc/g and an average pore diameter of 200 Å. The deposition of Pd and Au was carried out in two sequential steps. The impregnation of the palladium compound on alumina was carried out using the absorption technique of an organo palladium compound (acetylacetonate) in non-polar organic solvent on alumina. The contents of palladium and gold in the catalysts were in the range of 0.03 to 1 wt % and 0.003 to 0.3 wt %, respectively.

U.S. Pat. No. 4,762,956 discloses a novel catalyst and process for hydrogenation of dienes and acetylene impurities in an olefin feed. The catalyst is a palladium catalyst supported on substantially crystalline alpha alumina whose average pore radius is 200-2000 Å with at least 80% of pores having a pore radius within the range of 100 to 3000 Å. The active palladium metal surface was less than 50 m2/g with an average palladium particle size of at least 25 Å. The impregnation of palladium was carried out by spraying aqueous palladium chloride solution on alumina through an atomizer followed by drying at 80° C.

U.S. Pat. No. 5,866,735 discloses a hydrogenation process using a Pd catalyst supported on a support such as alumina, but modified with alkali iodide such as potassium iodide to reduced the formation of heavy products during the selective hydrogenation of diolefins and/or acetylenic compounds in mixed hydrocarbon streams.

U.S. Pat. No. 5,877,363 discloses the process for the selective hydrogenation of acetylenic impurities and isomerization of 1,2-butadiene to 1,3-butadiene in mixed olefin rich $C_4$ streams by using supported Pt, Pd, etc. catalyst.

European Patent No. 0 567 198 discloses Pd—Cu—K/$Al_2O_3$ catalyst for hydrogenation of alkynes and dienes. The preferred catalyst composition is 0.2% Pd, 0.3% Cu and 0.41% K. Preferred alumina support is $\gamma$-$Al_2O_3$ having 100-250 $m^2$/g surface area and 0.4-0.7 $cm^3$/g pore volume.

U.S. Pat. Nos. 4,644,088 and 4,658,080 disclose acetylene removal processes. The catalyst is multi component catalyst comprising at least Fe and Ni, other elements from Group 8, IB, IIB, IVB, VIB and VIIB of the Periodic Table, an alkaline earth metal and an alkali metal. The catalyst was prepared by mixing dry powders of $ZnFe_2O_4$, $BaCO_3$, and $NiCO_3$, followed by kneading the dry mix with aqueous NaOH solution and shaping to appropriate size pellets which were dried. The catalyst comprised a mixture of metal oxides, salts and hydroxides as prepared. The activated working catalyst appears to be mainly composed of metals and metal oxides. Aluminum oxide is not a part of this catalyst. The acetylenes are removed by contacting feeds with catalyst in vapor phase at a range of temperature from 250° to 900° C.

According to V. Rives et al., addition of Zn to Ni—Al Cr oxide catalyst for acetylene hydrogenation in mixed olefin stream hinders coke formation on the catalyst surface and the highest selectivity to ethylene is achieved for Zn/Ni atomic ratio of 4 (Applied Clay Science 13 (1998) 363-379).

A. Sarkany published a paper on egg-shell type Pd and Pd—Ag catalysts supported on alpha alumina for the hydrogenation of 1,3-butadiene (Applied Catalysis: General 175 (1998) 245-253). The deposition of low reactivity heavy hydrocarbons on the catalyst surface causes both the catalyst deactivation and over-hydrogenation to paraffinic products.

H. Uygur et al. published a paper (J. Chem. Eng. Japan, Vol. 31, No 2, 178 (1998)) concerning liquid phase selective hydrogenation of methylacetylene and propadiene (MAPD) in a mixed $C_3$ stream. They found that the conversion of MAPD over 0.3% Pd catalyst decreases as the hydrogenation temperature increases. S. D. Jackson et al. (App. Catalysis A: General 134 (1996) 91-99) found that the adsorption of phenyl acetylene increases with adsorption temperature during their study of the liquid-phase hydrogenation of phenyl acetylene and styrene on a palladium catalyst supported on carbon. N. R. M. Sassen et al. (Faraday Discuss. Chem. Soc., 89 (1998), 331-320) found that the adsorbed ethylidyne species on the Pd (111) increases as temperature raised from −20° C. to 0° C. We found that this is also true for the selective hydrogenation of $C_3$ and $C_4$ acetylenic compounds in a mixed crude butadiene stream over supported Pd—Ag catalyst. This seemingly strange behavior is the result of the combined effect of very low activation energy (<0.5 kcal/mole) of the selective hydrogenation, higher hydrogen solubility in the feed stream at lower temperature and temperature dependency of adsorption of acetylenic compounds on palladium surface in ternary phase reaction system of gas, liquid and solid catalyst. In other words, the concentration of hydrogen in the liquid phase is more influential on the selective hydrogenation rate of acetylenic compounds than the effect of apparent activation energy.

SUMMARY OF THE INVENTION

The present invention includes a supported catalyst comprising (1) Pd or a Group 8 metal comprising Pd and one other Group 8 metal, preferably a Group 8 metal selected from Pt, Ir, Ru, Co or Ni, and (2) at least two metals selected from Ag, Zn or Bi, preferably Ag and at least one of Zn or Bi. Optionally the catalyst may contain K. The content of K in the catalyst will normally be less than 0.5% by weight.

The process of hydrogenating unsaturated compounds by contacting hydrocarbon streams containing small amounts of acetylenic compounds with the catalyst of the invention in various arrangements and configurations is also part of the present invention The preferred supports are highly porous having average pore diameter larger than about 180 Å, no pores narrower than 35 Å, total pore volume larger than about 0.65 cc/g, and preferably less than about 100 m²/g BET surface area.

DETAILED DESCRIPTION OF THE INVENTION

This invention comprises an improved catalyst and a hydrocarbon hydrogenation process using the catalyst. Particularly the hydrogenation process pertains to the hydrogenation of multi unsaturated compounds such as acetylenic compounds and dienes to equivalent mono and di unsaturated products or saturated products depending on the purpose of process objective and hydrogenation of aromatic compound such as benzene to cyclic compound. The hydrogenation may be carried out in vapor phase, liquid phase and the existence of mixed phase of vapor and liquid. The hydrogenation may be carried out in any of a fixed bed reactor, trickle bed reactor, catalytic distillation reactor or any of combinations of these in the presence or absence of solvent. The examples of the preferred solvent are tetrahydrofuran, benzene, toluene, etc.

This invention is particularly useful in removing acetylenic compounds and dienes in $C_2$-$C_{12}$ organic compounds by selective hydrogenation to mono or di unsaturated or saturated organic compounds. The examples of such feed streams are steam cracked $C_2$, $C_3$, $C_4$, $C_5$, fractions or a mixed stream of $C_2$-$C_6$, and gasoline boiling range fuel.

The improved catalyst disclosed in this invention is multi component catalyst supported on highly porous supports such as alumina, silica, silica-alumina, carbon, etc. having total pore volume of at least 0.65 cm³/g and the average pore diameter of large than 180 Å. Alumina is the preferred support whose BET surface area is in a range of from 10 to 100 m²/g, preferentially 20 to 70 m²/g. The physical shapes of alumina may be spheres, pellets, granules, or extrudates whose size is in a range of from ¹⁄₃₂ to ¼ inches. The shaped alumina support will have the apparent bulk density (ABD) of less than 0.7 g/cm³, but no higher than that about 0.8 g/cm³. The alumina is a transition alumina having mixed crystalline forms of $\alpha$, $\kappa$, $\theta$, $\delta$, $\rho$, $\eta$, $\gamma$, and $\chi$, depending on calcination temperature and crystalline structure of raw material aluminum monohydrate. Alumina composed of mostly $\gamma$ or $\chi$ crystalline form are not preferred support. To prepare the preferred alumina, shaped alumina raw materials such as alumina gel or aluminum monohydrate are calcined at a temperature in a range of from about 650° to 1250° C. The final calcination temperature is determined by the physical properties of alumina support to obtain the best performance of catalyst for the specific hydrogenation process.

The preferred alumina disclosed in this invention can be prepared by a number of techniques well known to those skilled in art of preparing alumina. One of the preferred aluminas disclosed in this invention can be prepared by the so called oil dropping gelation techniques. The examples of the prior art are disclosed in U.S. Pat. Nos. 2,620,314; 4,273,735 and 4,179,408. The spherically shaped alumina is prepared from aluminum hydroxychloride sol prepared by digesting aluminum metal in aqueous hydrochloric acid solution. Spherical shaped alumina sol materials, produced in the form of droplets, are gelled in a basic liquid oil phase followed by aging, washing, drying, and calcining to the transition state aluminas at various temperatures depending on the desired property of alumina. Alternatively the preferred spherically shaped alumina can also be prepared by oil dropping gelation technique using the dispersed boehmite or pseudoboehmite alumina sols. The alumina sols are prepared by dispersing suitable boehmite, pseudoboehmite or mixtures of boehmite and pseudoboehmite aluminas obtained by hydrolyzing aluminum alkoxides and then crystallizing or reacting sodium aluminate solution with a solution of aluminum salt such as aluminum sulfate or aluminum nitrate and then crystallizing. Various boehmite aluminas or dispersed boehmite alumina sols are available in market place. Condea is one of the suppliers. To prepare the preferred spherical alumina whose physical properties are disclosed in this invention, Dispersal HP 14/2, Dispal 11N7-80, Dispal 23N4-20, Disperal HP 14, Deperal 40, Pural 200, Pural 100, Pural NG, etc. or mixtures of these can be used as raw materials. Other materials for the preparation of the preferred alumina support disclosed in this invention, because of too high surface area, too narrow pore diameter and too small pore volume. These materials yield the like aluminas disclosed in the U.S. Pat. Nos. 4,493,906 and 4,440,956. The preferred alumina in various extrudate or tablet forms can also be prepared by extruding the preferred boehmite or pseudoboehmite aluminas discussed above and calcining at elevated temperature from about 650° to about 1250° C. Optionally various structured packing materials made out of metals or ceramic materials for distillation column may be used as the support.

The content of K in the catalyst will normally be less than 0.5% by weight. The content of metals in the catalyst is Pd, preferably in a range of 0.005 to 1% by weight, more preferably from 0.01% to 0.3% by weight; Ni, preferably in the range of 0.0 to 15% by weight, more preferably from 0 to 10% by weight; Ag, preferably in the range of 0.002 to 20% by weight, more preferably 0.005 to 5% by weight; Zn, preferably in the range of 0 to 5% by weight, more preferably 0.002 to 1% by weight; and Bi, preferably in the range of 0 to 5% by weight, more preferably 0.01 to 3% by weight.

To deposit desired elements on a support, various techniques such as solution impregnation using rotary evaporator, incipient pore impregnation, spray-coating impregnation using atomizer, vapor deposition technique, co-precipitation techniques, etc. The preferred techniques in this invention are spray coating impregnation and incipient pore impregnation. Especially spray coating impregnation is the most preferred technique in this invention.

Depending on the objective of the specific hydrogenation reaction which determines what elements and how much are needed in the catalyst, a single impregnation or double impregnation is carried out. If Pd, Ag, and Zn are needed elements, a mixed solution of Pd, Ag, and Zn compounds in water or organic solvent is prepared. The solution is sprayed on the rolling support such as alumina in a rotary impregnator followed by drying with hot gas such as air or nitrogen at a temperature in a range of 60° C. to 300° C. The dried impregnation product is normally calcined at a temperature of from about 250° to 600° C. in air. If double impregnation is needed for the better catalyst performance, the first impregnation of a suitable support is carried out by incipient pore impregnation with an aqueous solution of a Zn compound, a mixed solution of Ag and Zn compounds or Pd, Ag, and Zn compounds, depending on specific performance objective of the catalyst. The impregnation product is dried at a temperature of from 60° C. to 300° C. followed by calcination at a temperature of 250° C. to 600° C. The second impregnation is carried out by spray coating impregnation with the second mixed solution of Pd and Ag or Pd, Ag, and Zn compounds on the first impregnation product with an atomizer followed by drying and calcination at a suitable temperature described above. For the most of selective hydrogenation reactions such as removal of acetylenic compounds in various mixed streams of olefins or dienes, the Pd penetration from the geometric outer surface of supports towards the interior of supports plays an important role in determining selectivity and stability of the catalyst. Less than 0.08 mm, preferentially less than about 0.06 mm Pd penetration is highly desirable. This objective can be accomplished by creating a fine liquid mist of the impregnation solution suspended in gas phase using a compressed gas atomizer. Also the volume of the liquid impregnation solution for a given amount of a support is important. The desired volume of the solution is less than about 85 volume %, preferably less than 65 volume % of total pore volume of the support.

When Bi is one of the desired components of the catalyst, the catalyst preparation may be carried out in one or two steps. For the single step impregnation, the impregnation of a mixed solution of Pd, Zn, Ag and Bi compounds on a support is carried out by either spray coating technique on rolling support inside of a rotary impregnator or incipient pore impregnation technique followed by drying and calcination as described earlier. If two step impregnation is desired, in the first step a solution of a Bi compound or a mixed solution of Bi and Zn compounds is used for either incipient pore impregnation technique or spray coating technique followed by drying and calcination at appropriate temperatures described earlier. Another alternative technique incorporating Bi or Bi and Zn into alumina support is impregnating a solution of Bi compound or a mixed solution of Bi and Zn compounds on uncalcined alumina followed by drying and calcining the impregnation product at a temperature in a range of from 650° C. to 1300° C. The second impregnation of a mixed solution of Pd, Ag, and Zn compounds or Pd, Ag, Zn and Bi compounds on the product from the first impregnation step is carried out by either spray coating impregnation or incipient pore impregnation followed by again drying and calcination as described earlier.

For the preparation of Zn or both Zn and Bi containing multi component catalyst, Zn or both Zn and Bi may be incorporated into the oil dropping gelation technique for the preparation of alumina support. The alumina support can be prepared by dropping alumina sol containing dissolved Zn compound or both Zn and Bi compounds into basic oil phase to form gel, followed by aging, washing, drying, and calcining at a temperature in a range of 650 to 1250° C. Optionally the alumina support may be prepared by impregnating a solution of Zn or Bi compound, or a mixed solution of Zn and Bi compounds on the alumina powders which have the physical characteristics of the preferred supports described earlier. The suitable raw materials preparing such alumina powders are boehmite powders and pseudoboehmite powders described earlier. The raw materials are calcined at temperatures from 350° to about 750° C. prior to the impregnation. The impregnation products are calcined at temperature from about 250° to 600° C., and then shaped to desired size of extrudates or pellets. Finally the shaped materials are calcined in air at an elevated temperature from about 650° to 1300° C. The mixed solution containing Pd and Ag compounds or Pd, Ag, And Zn compounds is impregnated on the so prepared alumina support by using one of impregnation techniques described earlier followed by drying and calcination.

The hydrogenation of unsaturated organic compounds is carried out with one or more catalysts. For the selective hydrogenation, one, two or more catalysts may be used to improve the yield of desired products. For example, the complete or near complete conversion of vinyl acetylene, ethyl acetylene, and methyl acetylene in a steam cracked butadiene stream, two or more catalysts, whose compositions and loading of metals are different, may be employed to obtain the highest quality product with the best economically desirable result. The catalysts may be loaded in a single reactor or two reactors. Higher activity catalyst is loaded in front of less active catalyst in a single reactor operation (fixed bed or catalytic distillation reactor operation) so that the feed stream is passed first through the higher activity catalyst zone. The hydrogen feed stream may be fed to the feed hydrocarbon stream at a single point prior to entering the catalytic reaction zone or fed to two or more different positions along the reactor to obtain the most desirable result, because usually two different activity catalysts have different optimal ratios of hydrogen to acetylenic compounds in feed at a given condition of concentration of a particular acetylenic compound, temperature, pressure and flow rate of hydrocarbons. If two reactors are used, higher activity catalyst is loaded in the first reactor.

The catalytic distillation hydrogenation is the preferred mode for selective hydrogenation of acetylenic compounds in various mixed streams to obtain the best selectivity and long catalyst life in the absence or presence of solvent. In the catalytic distillation hydrogenation, the polymer precursors and heavier polymers are continuously washed off by liquid phase and removed as a part of bottoms stream keeping the catalyst surface cleaner than fixed bed operation. Usually the selectivity of desired products is better than those of fixed bed operation, because higher concentrations of acetylenic compounds in the catalytic reaction zone can be kept by properly operating the distillation column reactor than can be achieved in the case of fixed bed operation. If a solvent is used, the catalytic distillation column may be operated in two ways. The distillation column may be operated in the total internal reflux mode for the solvent or the solvent may be fed to the top section of the column above the catalytic reaction zone and removed as a part of the bottoms stream depending on the boiling point of the solvent. The solvent recovered from the bottoms stream is recycled back to a position above the catalyst zone of the catalytic distillation column.

EXAMPLES

Control Example 1

The commercial eggshell type Pd—Ag catalyst supported on alumina (G681 obtained from UCI) was used to remove acetylenic compounds in a crude steam cracked butadiene stream. 36 grams of the commercial catalyst (0.2% Pd-0.1% Ag on alumina) were mixed with 100 ml of 3 mm diameter glass balls and loaded in a vertically mounted up-flow stainless reactor (1 inch diameter×20 inch long). The ABD of the catalyst was 0.97 g/cc. The average size of the catalyst is 2.5 mm diameter×6 mm long extrudate. The catalyst was activated at 230° F. by passing 1 ml/min (measured at ambient temperature) isobutane and 15 cc/min of hydrogen gas (10 volume % $H_2$ gas in He) under 200 psig for two hours. The reactor was cooled to the predetermined temperature and then the reactor pressure set to the predetermined pressure for hydrogenation. After shutting off both hydrogen and isobutane to the reactor, hydrocarbon feed and hydrogen while were slowly introduced while monitoring the reactor temperature. Due to exothermicity of the hydrogenation reaction, there may be a sudden temperature rise, if not careful, and the temperature at the beginning of the catalyst bed is lower than at the end of catalyst bed.

Acetylenic impurities in a mixed $C_4$ steam containing 570 ppm propyne, 6550 ppm vinyl acetylene, 1497 ppm ethyl acetylene, 55.47% 1,3 butadiene, 0.22% 1,2-butadiene and 15.41% 1-butene, etc. by weight were removed by carrying out selective hydrogenation over the activated G681 catalyst.

The improvements made in this invention over the prior art are higher throughput rate, higher quality of product stream, higher yield of desired product, and saving hydrogen.

Example 1

A spherical γ-alumina (2 mm diameter) was used to prepare a suitable support disclosed in this invention. The spherical γ-alumina is not a suitable support as it is, because of too high surface area and acidity. The physical properties of this alumina are listed in Table 1. The alumina was calcined at 1150° C. for 3 hours in air.

TABLE 1

| | |
|---|---|
| ABC, g/cc | 0.53 |
| Single-point BET, $m^2/g$ | 157.5 |
| Multiple-point BET, $m^2/g$ | 170.2 |
| Meso Pore Area, $m^2/g$ | 170.2 |
| Micro Pore Area, $m^2/g$ | 0 |
| Cumulative Adsorption Surface area, $m^2/g$ | 172.6 |
| Cumulative Desorption Surface area, $m^2/g$ | 230.4 |
| Total Pore Volume (cc/g) for pores less than 493 Å radius at P/P0 = 0.9801 | 0.912 |
| Cumulative Adsorption Pore Volume for pores (20-300 Å radius) | 0.852 |
| Cumulative Desorption Pore Volume for pores (17.5-300 Å radius) | 0.930 |
| Average Pore diameter, Å | 214.4 |

A mixed solution was prepared by dissolving 3.79 grams of $Zn(NO_3)_2.6H_2$), 0.52 grams of $AgNO_3$, and 13 grams of 10 wt % Pd nitrate in aqueous 10% $HNO_3$ solution in 100 grams of deionized water. This mixed solution was sprayed on the 300 grams of the calcined alumina by using a compressed air atomizer and rotary impregnator and dried with hot air at about 200° C. for 1 hour. The dried product was calcined at 350° C. for 2 hours. The calculated composition of this catalyst based on the amounts of chemicals used is 0.20% Pd/0.11% Ag/0.28% Zn by weight.

36 grams of this catalyst (Pd/Ag/Zn/Al2O3) was mixed with 100 ml of 3 mm diameter glass balls and loaded in the same reactor used in the control Example 1. The catalyst was activated in the following manner. The reactor was purged with a flow of 200 cc/min $N_2$ under 15 psig, slowly heated to 235° F., 100 cc/min a $H_2$ gas flow was cut into $N_2$ gas flow and hold for an hour. After shutting off $N_2$ gas, the hydrogen gas flow was increased to 300 cc/min and then the temperature was raised to 550° F. for 2 hours. The reactor was cooled in hydrogen gas flow to the desired hydrogenation reaction temperature. The reactor was flushed out with nitrogen (150 cc/min) and set to a predetermined pressure for hydrogenation reaction. The feed hydrocarbon and hydrogen feed gas were cut into the nitrogen stream slowly while monitoring the reactor temperature and slowly cutting out the nitrogen gas flow. The hydrocarbon feed was the same feed used in Control Example 1. The results of Control Example 1 and Example 1 are listed in Table 2.

It is clear from the results listed in Table 2 that the three component (Pd/Ag/Zn) catalyst supported on alumina has a superior performance over the conventional catalyst. The product quality in Example 1 is superior to the product in Control Example 1. The vinyl acetylene impurity in the feed in Example 1 is completely removed. Yet the recovery of 1,3-butadiene is better by more than 4% by weight. It is generally very rare that a high activity catalyst has higher yield of the desired product at equal or higher conversion than those of lower activity catalyst.

Example 2

The spherical γ-alumina used to prepare alumina support in Example 1 was calcined at 1100° C. for 3 hours in air.

A bismuth nitrate solution was prepared by dissolving 4.31 grams of $Bi(NO_3)_3.6H_2O$ in 285 ml deionized water acidified with six drops of concentrated nitric acid solution and incipient pore impregnation was carried out with this solution on 300 grams of above calcined alumina. The impregnation product was cold rolled for 10 minutes in a rotary impregnator and then dried with a hot air at about 200° C. for 1 hour. The dried product was calcined at 450° C. in air for 2 hours. A mixed solution was prepared by dissolving 3.79 grams of $Zn(NO_3)_2.H_2O$, 0.52 grams of $AgNO_3$ and 13.3 gram of 10 weight % palladium nitrate solution in 10% nitric acid solution in 100 ml deionized water. This mixed solution was sprayed on the above calcined product by using compressed air atomizer and rotary impregnator and then dried with hot air at about 200° C. for 1 hour. The dried product was calcined at 350° C. for 2 hours. The composition of this catalyst calculated based on the amounts of chemicals used is 0.20% Pd/0.11% Ag/0.27% Zn/1.42% Bi by weight.

36 grams of this catalyst ($Pd/Ag/Zn/Bi/Al_2O_3$) were mixed with 100 ml of 3 mm diameter glass balls and loaded in the same reactor used in Control Example 1. The catalyst was activated in the same manner in Example 1. The same hydrocarbon feed used in Control Example 1 and hydrogen stream were cut in slowly into nitrogen stream while watching the reactor temperature and slowly cutting off the nitrogen gas flow. The result is listed in Table 2.

TABLE 2

|  | Control | Example 1 | Example 1 | Example 2 |
|---|---|---|---|---|
| Temperature (° F.)* | 120 | 110 | 120 | 120 |
| Pressure (psig) | 108 | 125 | 108 | 108 |
| WHSV of HC feed | 4 | 3 | 4 | 6.1 |
| $H_2$ rate, scft/lb of HC | 1.34 | 1.56 | 1.34 | 1.31 |
| Product composition (ppm)** | | | | |
| VA | 85 | 36 | 0 | 0 |
| EZ | 278 | 159 | 91 | 0 |
| MA | 38 | 18 | 6 | 1 |
| Propadiene | 105 | 80 | 81 | 110 |
| 1,2-BD | 1322 | 1170 | 1212 | 1230 |
| Recovery† of 1,3-BD | 91.9 | 89.6 | 94.3 | 92.5 |

*Temperature at the end of the catalyst bed
**By weight $$^\dagger 1,3\text{-BD Recovery} = \frac{1,3\text{-BD wt \% in product} \times 100}{1,3\text{-BD wt \% in feed}}$$

The result clearly demonstrates the superior performance of the four component (Pd/Ag/Zn/Bi) catalyst supported on alumina disclosed in this invention over the prior art. All the $C_4$ acetylenic impurities in the feed are completely removed, even though the feed rate is 50% higher. Yet the recovery of 1,3-butadiene is superior to the prior art.

The invention claimed is:

1. A process for the selective hydrogenation of unsaturated compounds comprising contacting a feed containing unsaturated compounds comprising acetylenes, diolefins and olefins in at least partial liquid phase with hydrogen in the presence of a catalyst for the selective hydrogenation of unsaturated compounds comprising Pd or a Group 8 metal component comprising Pd and one other Group 8 metal, Ag in the range of 0.005 to 5% by weight, Zn in the range of 0.002 to 1% by weight and Bi in the range of 0.01 to 3% by weight to selectively hydrogenate acetylenes, diolefins, or olefins supported on shaped transition alumina having an apparent bulk density of between 0.7-0.8 g/cm$^3$ and having mixed crystalline forms of α, κ, θ, δ, ρ, η, γ, and χ, which is highly porous having average pore diameter larger than about 180Å, no pores narrower than 35 Å, total pore volume larger than about 0.65 cc/g, and BET surface area of 20 to 70 m$^{21}$/g.

2. The process according to claim 1 wherein said supported catalyst comprises a group 8 metal component comprising Pd and one other Group 8 metal.

3. The process according to claim 1 wherein said supported catalyst comprises a group 8 metal component selected from the group consisting of Pt, Ir, Ru, Co and Ni.

4. The process according to claim 1 wherein said supported catalyst comprises Pd.

5. The process according to claim 1 wherein said supported catalyst comprises K.

6. The process according to claim 5 wherein the content of K of said catalyst is less than 0.5% by weight.

7. The process according to claim 1 wherein said supported catalyst comprises Pd in the range of from 0.01% to 0.3% by weight.

8. The process according to claim 1 wherein said supported catalyst comprises Pd in the range of from 0.01% to 0.3% by weight and Ni in the range of from 0 to 10% by weight.

* * * * *